United States Patent
Gobin et al.

(10) Patent No.: US 9,061,050 B2
(45) Date of Patent: Jun. 23, 2015

(54) REPAIRING BRUCH'S MEMBRANE WITH HYDROGELS

(71) Applicant: University of Louisville Research Foundation, Inc., Louisville, KY (US)

(72) Inventors: Andrea S. Gobin, Louisville, KY (US); Tongalp H. Tezel, Louisville, KY (US)

(73) Assignee: UNIVERSITY OF LOUISVILLE RESEARCH FOUNDATION, INC., Louisville, KY (US)

(*) Notice: Subject to any disclaimer, the term of this patent is extended or adjusted under 35 U.S.C. 154(b) by 110 days.

(21) Appl. No.: 14/045,626

(22) Filed: Oct. 3, 2013

(65) Prior Publication Data
US 2014/0121161 A1 May 1, 2014

Related U.S. Application Data

(63) Continuation of application No. 13/642,063, filed as application No. PCT/US2011/033072 on Apr. 19, 2011, now abandoned.

(60) Provisional application No. 61/325,745, filed on Apr. 19, 2010.

(51) Int. Cl.
| | |
|---|---|
| *A61K 47/48* | (2006.01) |
| *A61K 9/00* | (2006.01) |
| *A61K 45/06* | (2006.01) |
| *A61K 38/07* | (2006.01) |
| *A61K 38/08* | (2006.01) |
| *A61K 31/78* | (2006.01) |
| *A61K 9/06* | (2006.01) |
| *A61K 38/18* | (2006.01) |
| *A61L 27/18* | (2006.01) |
| *A61L 27/22* | (2006.01) |
| *A61L 27/52* | (2006.01) |
| *A61L 27/54* | (2006.01) |
| *A61K 38/30* | (2006.01) |

(52) U.S. Cl.
CPC ............ *A61K 31/78* (2013.01); *A61K 9/0048* (2013.01); *A61K 9/06* (2013.01); *A61K 38/07* (2013.01); *A61K 38/08* (2013.01); *A61K 38/18* (2013.01); *A61K 47/48215* (2013.01); *A61K 47/48784* (2013.01); *A61L 27/18* (2013.01); *A61L 27/227* (2013.01); *A61L 27/52* (2013.01); *A61L 27/54* (2013.01); *A61L 2300/414* (2013.01); *A61L 2300/416* (2013.01); *A61L 2300/426* (2013.01); *A61L 2430/16* (2013.01); *A61K 38/1808* (2013.01); *A61K 38/1825* (2013.01); *A61K 38/1858* (2013.01); *A61K 45/06* (2013.01); *A61K 38/30* (2013.01)

(58) Field of Classification Search
None
See application file for complete search history.

(56) References Cited

U.S. PATENT DOCUMENTS

2013/0084262 A1    4/2013  Gobin et al.

OTHER PUBLICATIONS

Gonzalez, et al. Integrin Interactions with Immobilized Peptides in Polyethylene Glycol Diacrylate Hydrogels, Tissue Engineering 10(11/12): 1775-1786, 2004.*
Singh et al. Biomaterials. 22: 3337-3343, 2001.*
Benoit, "The effect on osteoblast function of colocalized RGD and PHSRN epitopes on PEG surfaces", Biomaterials 26, 5209-5220 (2006).
DeLong, "Covalently immobilized gradients of bFGF on hydrogel scaffolds for directed cell migration", Biomaterials 26, 3227-3234 (2005).
Gobin et al., "Cell migration through defined, synthetic ECM analogs", FASEB J., 16, 751-753, 2002.
Gobin, "Val-Ala-Pro-Gly, an elastin derived non-integrin ligand: cell adhesion and specificity", Engineering in Medicine and Biology, 24th Annual Conference and the Annual Fall Meeting of the Biomedical Engineering Society EMBS/BMES Conference, Proceedings of the Second Joint, vol. 1, 866-867, 2002.
Gombotz et al., "Protein adsorption to poly(ethylene oxide) surfaces", J. Biomed. Mater. Res., 25, 1547-1562, 1991.
Gonzalez et al., "Integrin Interactions with Immobilized Peptides in Polyethylene Glycol Diacrylate Hydrogels", Tissue Engineering, vol. 10, No. 11/12, 1775-1786, 2004.
Hern et al., "Incorporation of adhesion peptides into nonadhesive hydrogels useful for tissue resurfacing", Journal of Biomedical Materials Research, 39, 266-276, 1998.
Hubbell et al., "Surface-grafted Cell-binding Peptides in Tissue Engineering of the Vascular Graft", Ann NY Acad Sci, 665, 253-258, 1992.
Kizilel et al. "Photopolymerization of Poly(Ethylene Glycol) Diacrylate on Eosin-Functionalized Surfaces", Langmuir 20, 8652-8658 (2004).
Mann et al., "Tethered-TGF-β increases extracellular matrix production of vascular smooth muscle cells", Biomaterials, 22, 439-444, 2001.
Mann et al., "Smooth muscle cell growth in photopolymerized hydrogels with cell adhesive and proteolytically degradable domains: synthetic ECM analogs for tissue engineering", Biomaterials, 22, 3045-3051, 2001.
Merrill et al., "Polyethylene Oxide as a Biomaterial", 1983. ASAIO Journal, 6, 60-64, 1983.
O'Shea, "Age-related macular degeneration", Postgrad. Med. J., 74, 203-207, 1998.

(Continued)

*Primary Examiner* — Amber D Steele
*Assistant Examiner* — Schuyler Milton
(74) *Attorney, Agent, or Firm* — Viksnins Harris & Padys PLLP

(57) ABSTRACT

The invention provides hydrogels and methods for their use in treating disorders of the retina such as age-related macular degeneration (AMD).

16 Claims, 8 Drawing Sheets

(56) References Cited

OTHER PUBLICATIONS

Patent Cooperation Treaty, International Searching Authority, Search Report and Written Opinion for PCT/US2011/033072, 12 pages, dated Feb. 8, 2012.

Tezel et al., "Reattachment to a substrate prevents apoptosis of human retinal pigment epithelium", *Graefes Arch Clin Exp Ophthalmol.*, 235(1), 41-47, 1997.

Tezel et al., "Reengineering of Aged Bruch's Membrane to Enhance Retinal Pigment Epithelium Repopulation", *Invest Ophthalmol. Vis. Sci.*, 45(9), 3337-3348, 2004.

* cited by examiner

Figure 1
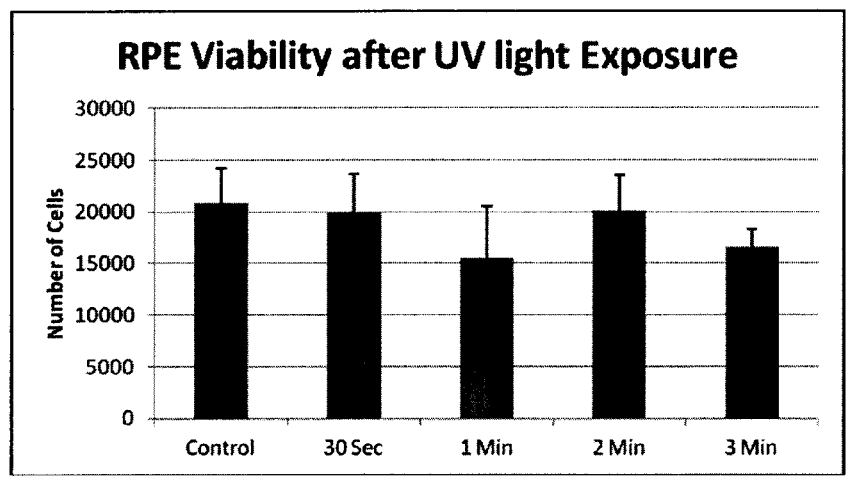
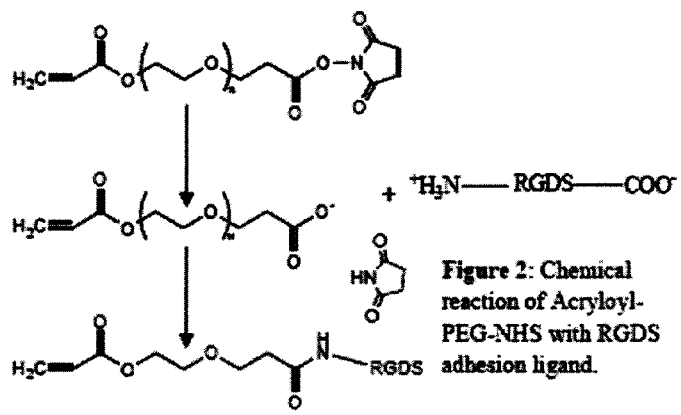
Figure 2: Chemical reaction of Acryloyl-PEG-NHS with RGDS adhesion ligand.

Figure 9
A
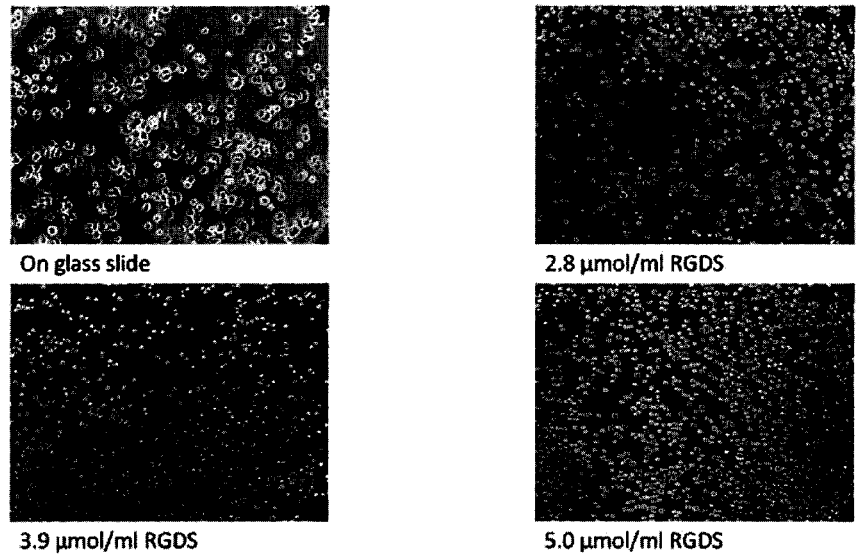
B
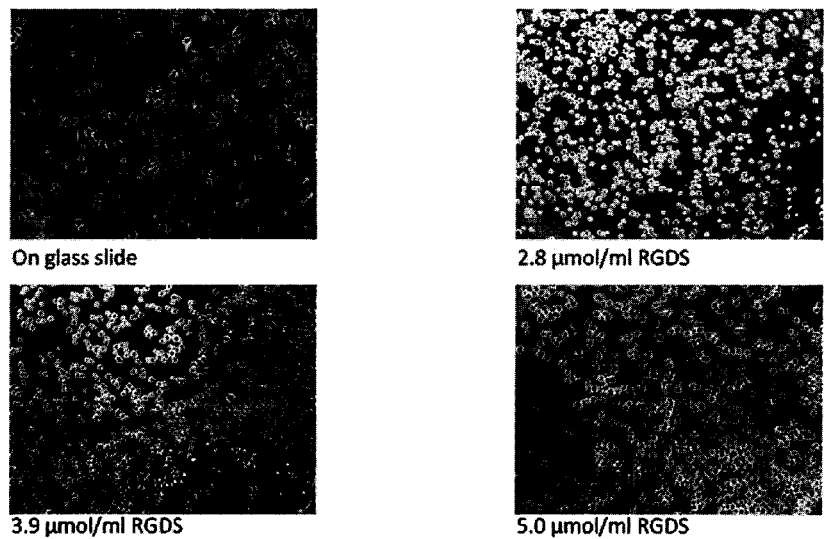

REPAIRING BRUCH'S MEMBRANE WITH HYDROGELS

CROSS-REFERENCE TO RELATED APPLICATION(S)

This application is a continuation application of U.S. patent application Ser. No. 13/642,063, which is a U.S. 371 application of PCT/US2011/033072, filed 19 Apr. 2011, and claims the benefit of priority of U.S. Ser. No. 61/325,745, filed 19 Apr. 2010, the entirety of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 26, 2013, is named 17541.077US1_SL.txt and is 1,912 bytes in size.

BACKGROUND

Age-related macular degeneration (AMD) is a disease that results in loss of central vision due to damage to the macula, the center part of the retina. AMD occurs in two different stages: dry and wet stages. The dry stage, the more common of the two, occurs when the light-sensitive tissues of the macula becomes thin and slowly lose function. The wet stage is caused by the growth of abnormal retinochoroidal blood vessels underneath the retina which rupture the Bruch's membrane. Although several anti-angiogenic treatments have been employed for wet AMD, the resultant fibrovascular scar almost always causes loss of sight. Thus, more effective treatments for wet AMD are required. Currently, there are no treatments for dry AMD. Accordingly, treatments for AMD are needed.

SUMMARY OF CERTAIN EMBODIMENTS OF THE INVENTION

Certain embodiments of the invention provide a polymerizable, e.g., an in situ polymerizable, poly(ethylene glycol) (PEG) based diacrylate hydrogel that comprises at least one adhesion ligand.

In certain embodiments, at least one adhesion ligand is covalently attached to the PEG hydrogel through a PEG linker chain.

In certain embodiments, at least one adhesion ligand comprises the amino acid sequence RGDS (SEQ ID NO:1), YIGSR (SEQ ID NO:2), KQAGDV (SEQ ID NO:3), RGDV (SEQ ID NO:4), RGD-HYP (hydroxyproline) (SEQ ID NO:5), RGDT (SEQ ID NO:6) or VTCG (SEQ ID NO:7).

In certain embodiments, at least one adhesion ligand is the amino acid sequence RGDS (SEQ ID NO:1), YIGSR (SEQ ID NO:2) or KQAGDV (SEQ ID NO:3).

In certain embodiments, at least one adhesion ligand is the amino acid sequence RGDS (SEQ ID NO:1).

In certain embodiments, the concentration of the adhesion ligand is about 5.0 μmol/ml.

In certain embodiments, the hydrogel further comprises PHSRN (SEQ ID NO:8).

In certain embodiments, at least one adhesion ligand is the amino acid sequence YIGSR (SEQ ID NO:2).

In certain embodiments, the hydrogel further comprises at least one growth factor.

In certain embodiments, the growth factor is bFGF, PDGF, hepatocyte growth factor (HGF), insulin-like growth factor (IGF) or epidermal growth factor (EGF).

In certain embodiments, the hydrogel further comprises an anti-angiogentic or anti-apoptotic drug or cytokine.

In certain embodiments, the hydrogel is suitable for injection.

In certain embodiments, the hydrogel is a photopolymerizable hydrogel.

Certain embodiments of the invention provide a method for preparing a hydrogel, comprising:
a) combining a PEG diacrylate with an acryloyl-PEG-adhesion ligand and/or an acryloyl-PEG-growth factor in an appropriate solution;
b) filter sterilizing the solution; and
c) adding a photoinitiator to the solution.

In certain embodiments, the photoinitiator is 2,2-dimethyl-2-phenyl-acetophenone in n-vinylpyrrolidone.

In certain embodiments, the method further comprises exposing the solution prepared in step c) to UV light.

Certain embodiments of the invention provide hydrogel prepared according to the methods described herein.

Certain embodiments of the invention provide a hydrogel described herein for use in therapy.

Certain embodiments of the invention provide a hydrogel described herein for use in treating a disorder of the retina.

Certain embodiments of the invention provide a hydrogel described herein for use in medical treatment.

Certain embodiments of the invention provide the use of a hydrogel as described herein to prepare a medicament useful for treating a disorder of the retina in an animal.

In certain embodiments, the disorder of the retina is age-related macular degeneration (AMD), choroidal ruptures, angioid streaks, myopic maculopathy, presumed ocular histoplasmosis, globe ruptures, penetrating injuries, RPE and retinal atropies, degeneration or dystrophy.

In certain embodiments, the disorder of the retina is AMD.
In certain embodiments, the AMD is wet AMD.
In certain embodiments, the AMD is dry AMD.

Certain embodiments of the invention provide a method for treating a disorder of the retina in a patient in need of such treatment, comprising administering to the patient a therapeutically effective amount of a hydrogel as described in herein and polymerizing the hydrogel with UV light.

In certain embodiments, the methods further comprises performing a vitrectomy on the patient to remove subretinal scars.

The Bruch's membrane has 5 layers, including the basement membrane of the retinal pigment epithelium (RPE). Several metabolites and oxygen are transported through Bruch's membrane, which are vital for the physiological functions of the retinal cells. In aging, Bruch's membrane becomes thickened and does not allow the metabolites to diffuse easily. Initial steps of treating wet AMD involve removal of the fibrovascular scar tissue. Although surgical excision of the subfoveal neovascular tissue is not necessarily technically challenging, it usually results in removal of the neighboring RPE cells and adherent layers of the Bruch's membrane. At the end of the surgery, an uneven surface of Bruch's membrane is exposed onto which newly seeded RPE cells can not attach and proliferate. Several age-related structural changes within the Bruch's membrane make it inhabitable to RPE cells. Thus, rejuvenation of the molecular structure of the aged-Bruch's membrane may allow RPE cells to attach and resurface the aged Bruch's membrane. However, the uneven surface of the Bruch's membrane has to be repaired to create a uniform layer that can subsequently allow RPE cells to attach and proliferate. As disclosed herein, such repair can be made with a biogel that can fill the uneven surface. This biogel is a poly(ethylene glycol) (PEG) hydrogel that can be enriched with molecules/ligands that assist in the anchoring, flattening, proliferating and surfacing of RPE cells. This specially formulated photopolymerizable PEG hydrogel can be used to enhance RPE survival and surfacing of the Bruch's membrane defects in both wet and dry AMD, as well as other hereditary, degenerative and traumatic disease of the retina where RPE, Bruch's membrane and/or sensory retinal cell loss is aimed to be repaired with tissue engineering techniques.

Thus, in certain embodiments, a method is provided for repairing subretinal choroidal neovascularization defects of the Bruch's membrane secondary to wet AMD or other clinical conditions, such as degenerative myopia, angioid streaks, inflammatory chorioretinal diseases, trauma or idiopathic choroidal neovascularization. The method is useful to treat conditions in which the integrity of the subretinal space has been disrupted. The method may include a one-time surgery (vitrectomy) to remove subretinal scars, sealing defects of Bruch's membrane, utilizing the hydrogel in situ repair system and restoring the deranged subretinal anatomy by cell transplantation techniques to recover central vision described herein.

Accordingly, described herein is an injectable hydrogel system that can be polymerized in situ following, e.g., surgical removal of the choroidal neovascular complex, to promote RPE repopulation into the defective region to restore central sight. Previously, several natural or artificial scaffolds have been proposed to transplant cells and/or cover the defects of the Bruch's membrane. However, these scaffolds fail to cover uneven defects of the Bruch's membrane and can not integrate to the residual collagen matrix. Thus, once overlying RPE cells contract, they typically detach from the native Bruch's membrane and crumble upon themselves, leading to the failure of the RPE graft. By filling the uneven defects of the Bruch's membrane and creating a vertical stability, the use of injectable hydrogel overcomes limitations previous studies encountered and provides a reconstructive surgery method for restoring sight in patients with AMD and hereditary, degenerative and traumatic disease of the retina that are characterized by RPE, Bruch's membrane and/or sensory retinal cell loss.

BRIEF DESCRIPTION OF THE FIGURES

FIG. 1: Cell viability after exposure to UV light, 365 nm, for 0.5, 1, 2, 3 minutes. Data is average with standard deviation.

FIG. 2: A reaction of acryloyl-PEG-NHS with an adhesion ligand. "RGDS" disclosed as SEQ ID NO: 1.

FIG. 9: RPE adhesion after 30 minutes (9A) and after two hours 9(B) with different concentrations of RGDS (SEQ ID NO:1).

DETAILED DESCRIPTION

Figure 3:
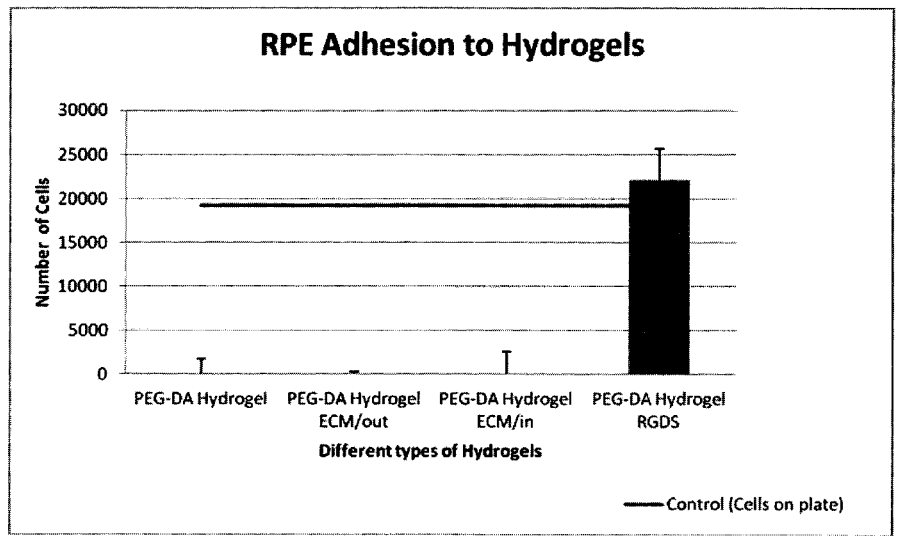
FIG. 3: Retinal pigment epithelium (RPE) attachment to PEG hydrogels with or without RGDS (SEQ ID NO:1) or with extracellular matrix protein (ECM-P) cocktail coated or incorporated. Results are averages with standard deviations.

The categorized stages of AMD are early, in which visual symptoms are not easily seen; and late, in which severe visual loss is common. Late AMD can exist in either geographic atrophy (dry) or exudative (wet) forms. The dry form of AMD causes vision loss through the depletion of photoreceptors and RPE cells, which support the photoreceptors in the central part of the eye. Unfortunately, there are no current treatments available for dry AMD. An initial sign of exudative AMD is a serous or hemorrhagic fluid that causes the neuroretina or RPE (a central element in the pathogenesis of AMD) to detach from Bruch's membrane. The RPE serves several functions including regeneration of the bleached visual pigments, formation and maintenance of the extracellular matrix (interphotoreceptor matrix and Bruch's membrane), transport of fluids and ions between photoreceptors and the choriocapillaris, and phagocytosis. The RPE adheres to Bruch's membrane, a pentilaminar acellular structure, composed of a central elastin membrane, surrounded by collagen layers. The inner collagen layer is sub-adjacent to the basal lamina layer, which is the basement membrane of the RPE. The basement membrane of the choriocapillaris borders the outer collagen layer and Bruch's membrane functions as an intercellular matrix supporting and regulating cells from both the RPE and choriocapillaris.

Aging of Bruch's membrane in humans causes numerous structural changes such as increased thickness, deposition of extracellular matrix and lipids, collagen cross-linking, elastin fragmentation and formation of advanced glycation end products. In addition, the layers of Bruch's membrane do not remain intact after submacular membranectomy in AMD patients. Studies have shown that RPE surfacing of the aged Bruch's membrane following surgical excision of the fibrovascular membrane is not possible due to age-related changes affecting RPE cell attachment and survival. In vivo studies on RPE defects, when Bruch's membrane was not damaged, showed complete and rapid wound healing. In addition, studies that investigated fragmentation of Bruch's membrane also found the defects to be fully resurfaced after 7 days, with cells proliferating from the edge and within the defect. However, the newly formed RPE surface regressed four weeks later, which may have been due to the inability of the degenerate choriocapillaris to support the newly ingrown RPE. In vitro RPE wound healing studies on human explants demonstrated that RPE adhesion, proliferation and migration on aged Bruch's membrane with intact basal lamina was similar to normal resurfacing patterns seen in vivo. However, when deeper layers of Bruch's membrane were exposed, RPE repopulation decreased with increased apoptosis rates. Thus, resurfacing of Bruch's membrane is dependent on the layer of the membrane available for RPE cell attachment and the presence of age-related changes within Bruch's membrane.

Current clinical therapies for AMD include thermal laser photocoagulation, photodynamic therapy and recently introduced anti-vascular endothelial growth factor (VEGF) pharmacotherapy. Though these therapies can temporarily stabilize and increase the visual acuity, they do not address the underlying pathology or remain palliative. For example, more than 50% of patients do not respond to anti-VEGF therapy, or develop subretinal scars that limit the visual gain. Recent research has indicated that patients with late stage disciform scars have the potential to recover vision if the subretinal architecture is reconstituted (Del Priore et al., *Progress in Retinal and Eye Research*, 25, 539-562 (2006)). Although retinal cell transplantation studies were initiated almost a decade ago, all were unsuccessful primarily due to the failure of the aged Bruch's membrane to support the attachment and subsequent survival of the retinal pigment epithelial (RPE) grafts. Reconstructing the aged Bruch's membrane may restore human RPE cell function on this aged matrix. Hence, it is proposed herein that reconstructing the deranged subretinal milieu in AMD, to transplant allograft RPEs, or enable migration of the surrounding native RPE, may provide a critical component in restoring sight. Several different artificial matrices have been tried as a support for the transplanted RPE cells. However, these solid structure failed to cover uneven defects of the Bruch's membrane, often remain undulated and did not remain attached to the underlying remnant of the Bruch's membrane.

A poly(ethylene glycol) (PEG) based hydrogel, which can fill in the uneven defects of the Bruch's membrane, adhere strongly to residual collagen framework and create an even surface for cell population, is described herein. This hydrogel will also be useful for treating defects in the extracellular matrices in various organs other than the Bruch's membrane and can be useful for treating diseases related with aging or defective extracellular matrices, such as atherosclerosis, emphysema, glomerulosclerosis or Alzheimer's. This gel can be formulated to contain optimum amounts of extracellular anchoring molecules and/or growth factors for RPE cell survival and resurfacing. Furthermore, other chemicals and drugs can be incorporated into the gel, and it can be used as a reservoir for the treatment of the condition that necessitates subretinal surgery. Such medications include, but not limited to, anti-angiogenic and anti-apoptotic drugs and cytokines. Thus, the hydrogel can be used to stimulate RPE cells to re-epithelialize the aged Bruch's membrane. The hydrogel is an injectable, minimally invasive, biomimetic, in situ polymerizable substrate that can fill-in defects of aged Bruch's membrane for reconstitution of the subretinal space.

Described herein is a biomimetic hydrogel based on acrylate derivatives of poly (ethylene glycol) (PEG) that can be utilized to repair uneven defects of aged Bruch's membrane and stimulate RPE population. The product can be an in situ photopolymerizable hydrogel in which cell adhesion peptides, such as RGDS (SEQ ID NO:1), YIGSR (SEQ ID NO:2), KQAGDV (SEQ ID NO:3), and growth factors, such as platelet derived growth factor (PDGF) and fibroblast growth factor (FGF), or various pharmacological agents, such as anti-angiogenic molecules, antibodies or anti-metabolites can be grafted into the hydrogel, to promote interaction with specific cell surface receptors and/or modulate cellular behavior. In situ polymerization can be accomplished through the use of ultraviolet light (UV; $\lambda$=365 nm) delivered through fiber optics. The formulation of the gel allows it to polymerize at exposure levels that are safe for the resident and transplanted cells.

PEG hydrogels were selected due to PEG's hydrophilicity, biocompatibility, and intrinsic resistance to protein adsorption and cell adhesion. These hydrogels can be rendered bioactive by the incorporation of biosignals, such as adhesion ligands and growth factors. To support cell adhesion and growth, adhesion peptide ligands derived from matrix proteins can grafted into the hydrogel (Herr et al., *Journal of Biomedical Materials Research*, 39, 266-276 (1998); Mann et al., *Biomaterials*, 22, 439-444 (2001); Gobin et al., *FASEB J.*, 16, 751-753 (2002); and Hubbell et al., *Ann NY Acad Sci*, 665, 253-258 (1992)). These short sequences (e.g., 3, 4, 5, 6, 7, 8, 9, or 10 amino acids in length) are advantageous due to their stability, and their synthetic nature renders them more receptive to chemical derivatization. Incorporation of adhesion ligands at various concentrations can affect not only cell adhesion morphology, but also cellular processes such as cell migration. It has been discovered that RGDS (SEQ ID NO:1) can be grafted into the hydrogels and support RPE adhesion and proliferation. A significant increase in the number of cells adhered as compared to hydrogels without RGDS (SEQ ID NO:1) has been demonstrated. After adhesion, the cells were able to proliferate.

An overall goal of the research described herein was to design and develop an in situ polymerizable, biomimetic hydrogel, prepared with concentrations of adhesion ligands for cell attachment and growth factors for promoting cell growth, to stimulate RPE wound healing and macula regeneration.

The technology described herein thus includes methods to reconstruct the deranged anatomy of the subretinal space using advanced bioengineering methods and can be applied to several other chorioretinal and vitreal diseases where subretinal architecture disruption results in vision loss. The technology includes a base poly ethylene glycol (PEG) diacrylate with incorporated biochemical signals, such as adhesion ligands and growth factors. Because the system can be in situ polymerizable, the technology can be applied to various wounds or to deranged substratum sizes and shapes. In certain embodiments, the methods can also include delivery of drugs, such as anti-VEGF therapy drugs, to enhance the success of the surgery. In addition, the material can be designed to be degradable.

One application for this technology is to treat age-related macular degeneration. Other retinal hereditary, degenerative and traumatic diseases and disorders that this technology can be used to treat include but not limited to are choroidal ruptures, angioid streaks, myopic maculopathy, chorioretinal inflammatory diseases such as presumed ocular histoplasmosis, globe ruptures and penetrating injuries, RPE and retinal atropies, degenerations and dystrophies.

Poly ethylene glycol hydrogels are biocompatible and resist protein adsorption (Merrill et al., *ASAIO J*, 6, 60-64 (1983) and Gombotz et al., *J Biomed Mater Res*, 25, 1547-62 (1991)). Experiments conducted to date include assessment of viability of RPE after exposure to a UV light source and initial RPE adhesion and early proliferation studies.

Accordingly, certain embodiments provide an in situ polymerizable poly(ethylene glycol) (PEG) based hydrogel that comprises at least one adhesion ligand and/or at least one growth factor.

In certain embodiments, the hydrogel is a photopolymerizable hydrogel.

In certain embodiments, the at least one adhesion ligand comprises the amino acid sequence RGDS (SEQ ID NO:1), YIGSR (SEQ ID NO:2), KQAGDV (SEQ ID NO:3), RGDV (SEQ ID NO:4), RGD-HYP (hydroxyproline) (SEQ ID NO:5), RGDT (SEQ ID NO:6), or VTCG (SEQ ID NO:7).

In certain embodiments, the at least one adhesion ligand is the amino acid sequence is RGDS (SEQ ID NO:1), YIGSR (SEQ ID NO:2), KQAGDV (SEQ ID NO:3), RGDV (SEQ ID NO:4), RGD-HYP (hydroxyproline) (SEQ ID NO:5), RGDT (SEQ ID NO:6), or VTCG (SEQ ID NO:7), e.g., RGDS (SEQ ID NO:1).

In certain embodiments, the growth factor is bFGF, PDGF, hepatocyte growth factor (HGF), insulin-like growth factor (IGF) or epidermal growth factor (EGF).

In certain embodiments, the hydrogel comprises at least one adhesion ligand and at least one growth factor.

In certain embodiments, the hydrogel comprises an anti-angiogentic or anti-apoptotic drug or cytokine.

In certain embodiments, the hydrogel is suitable for injection.

Certain embodiments provide a hydrogel as described herein for use in therapy.

Certain embodiments provide a hydrogel as described herein for use in treating a disorder of the retina.

Certain embodiments provide a hydrogel as described herein for use in medical treatment.

Certain embodiments provide the use of a hydrogel as described herein to prepare a medicament useful for treating a disorder of the retina in an animal.

Certain embodiments provide a method for treating a disorder of the retina in a patient in need of such treatment, comprising administering to the patient a therapeutically effective amount of a hydrogel as described herein to the patient.

Certain embodiments provide a method for treating a disorder in which the integrity of the subretinal space has been disrupted in a patient in need of such treatment, comprising administering to the patient a therapeutically effective amount of a hydrogel as described herein to the patient.

In certain embodiments, the disorder is age-related macular degeneration (AMD), choroidal ruptures, angioid streaks, myopic maculopathy, presumed ocular histoplasmosis, globe ruptures, penetrating injuries, RPE and retinal atropies, degeneration or dystrophy.

In certain embodiments, the disorder is AMD.

In certain embodiments, the disorder is dry AMD.

In certain embodiments, the disorder is wet AMD.

In certain embodiments, the method further comprises performing a vitrectomy on the patient to remove subretinal scars.

SUMMARY OF CERTAIN RESULTS

To briefly summarize certain finding, PEGDA hydrogels (and sub components thereof) are non-toxic to RPE cells and photoreceptors. RPE and photoreceptors were exposed to various components of the hydrogel formation process and found to be viable after exposed of minutes. Photopolymerization typically occurs 30-60 seconds after exposure, but to be certain the entire volume is polymerized, there is overlap in exposure areas, thus increasing the exposure to reagents and UV light to a few minutes. No significant death was seen from this increased exposure time. Other crosslinking energy sources were investigated as possible alternatives. Rose Bengal and eosin Y were both investigated, but found to significantly increase the reaction time, thus increasing risk and possible further surrounding tissue damage.

Within the initial 24 hours, RPE cells attach and remain viable on hydrogel surfaces that contain 5.0 µmol/ml adhesion peptide (e.g., RGDS (SEQ ID NO:1)). Concentrations below 5.0 µmol/ml still enhance adhesion on PEGDA, however, 5.0 µmol/ml has the quickest and most efficient adhesion rate. When compared to over ECM-P molecules presented in the hydrogels, the attachment rate was also significantly better on the hydrogels with RGDS (SEQ ID NO:1) alone. This is because the ECM-P cocktail does not adsorb to the PEGDA hydrogels. Since the cocktail can diffuse away from the scaffold, there are not attachment sites for the cells to adhere to.

Once cells have adhered to the surface of the hydrogels with RGDS (SEQ ID NO:1) adhesion ligand, cells were capable of proliferating. This was assessed 48 hrs after initial adherence. It was observed that cells could proliferate on the hydrogels with RGDS (SEQ ID NO:1). Cells on higher concentrations of adhesion ligand proliferated more quickly.

In order to improve the success of cell transplantation, cell adhesion rate within the initial surgery time was investigated (30 minutes-2 hours). It was initially observed that concentrations above 5 µmol/ml of RGDS (SEQ ID NO:1) did not significantly increase the amount of adhesion.

In order to be certain all cells transplanted are in the correct location during surgery, magnetic beads were investigated as a tool for cell delivery. It was observed that the combination of beads with the UV light did not significantly impair the viability of the cells. However if cells were placed within the prepolymer solution before crosslinking, the beads were unable to move them through the solid hydrogel to the correct location. Cells would thus have to be transplanted after the defect is filled with the hydrogel material. Since hydrogel is non-degradable, cells cannot migrate though and disrupt the engineered organization of the materials and transplanted cells.

Thus, the methodology described herein can be used to repair and repopulate aged matrices all over the body. Thus, it may be used for the treatment of several disorders associated with aged-matrices in the body, such as Alzheimer's disease, glomerulosclerosis, atherosclerosis, emphysema and skin wrinkling. The technology is an improvement as it demonstrates mending irregular defects of an extracellular matrix with a liquid gel that may fill in the cavities and create an even surface for the cells to attach and spread. Before this discovery, several researchers have used various scaffold to support and transplant cells. However, vertical stability of these scaffolds on the damaged host Bruch's membrane was never thought of. Thus, due to their contractile properties, RPE cells almost always pull these matrices, which resulted in failure of the graft. Described herein is a substrate that fills in and strongly adheres to residual Bruch's membrane creating a habitable even surface for the seeded cells. Hydrogels may be used to carry several pharmacological agent that help to promote cell survival in the subretinal space as well as to inhibit recurrence of choroidal neovascular membrane ingrowth.

9

These agents can be anti-apoptotic drugs, anti-angiogenic drugs, e.g., anti-VEGF agents, or cytokines that modulate cell behavior.

The invention will now be illustrated by the following non-limiting Examples.

Example 1

Viability of Retinal Pigment Epithelium

Objective:
To assess if retinal pigment epithelium (RPE) are viable after exposure to UV light source.
Protocol:
RPE cells were seeded into 96 well plates and allowed to adhere. They were exposed to UV light (365 nm, 7 cm away from source, ~10 mW·cm$^2$) for 30 seconds, 1, 2 and 3 minutes. Hydrogel polymerization occurs typically in 30-90 seconds. Cell viability was determined using a MTS assay.
Results:
No statistical difference was observed between cells exposed to UV light source or none (FIG. 1).

Example 2

RPE Adhesion and Proliferation on Hydrogels

Figure 4:
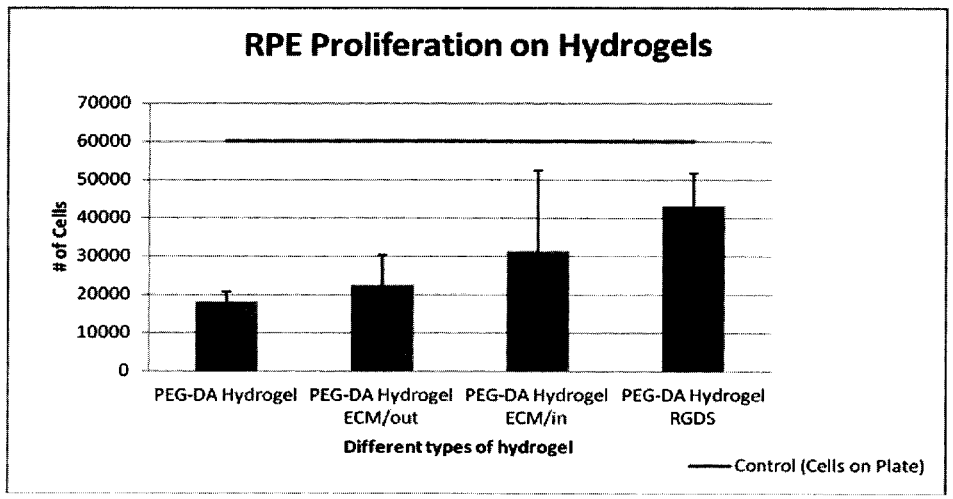
FIG. 4: RPE proliferation to PEG hydrogels with or without RGDS (SEQ ID NO:1) or with ECM-P cocktail coated or incorporated. Results are averages with standard deviations.
Figure 5:
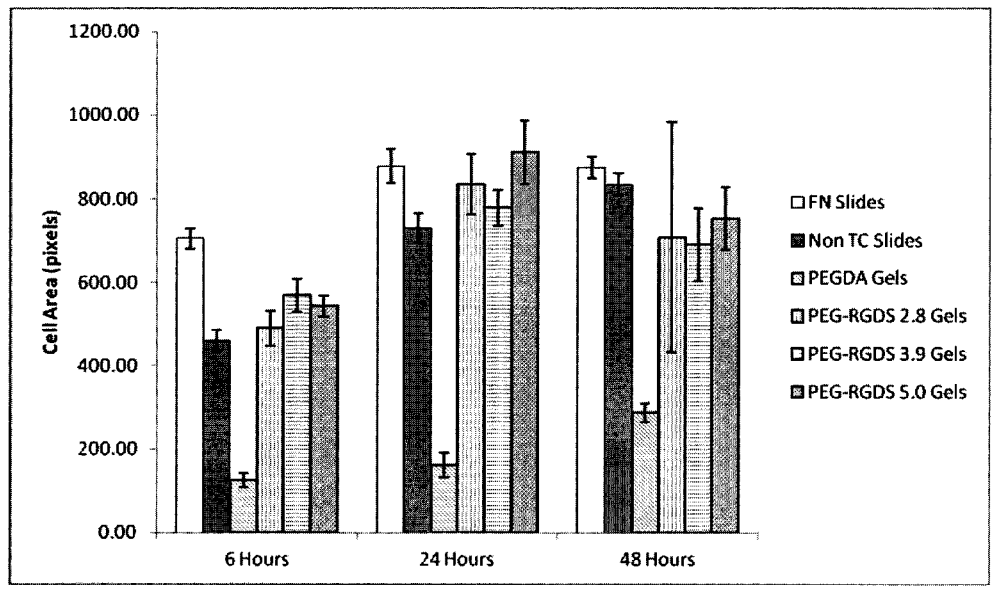
FIG. 5: Cell area of RPE after 6, 24, or 48 hours incubation. Hydrogels contained 2.8, 3.0, 5.0 μmol/mL of RGDS (SEQ ID NO:1). Controls included no RGDS (SEQ ID NO:1) adhesion ligands, non-tissue culture surfaces or surfaces treated with fibronectin.
Figure 6:
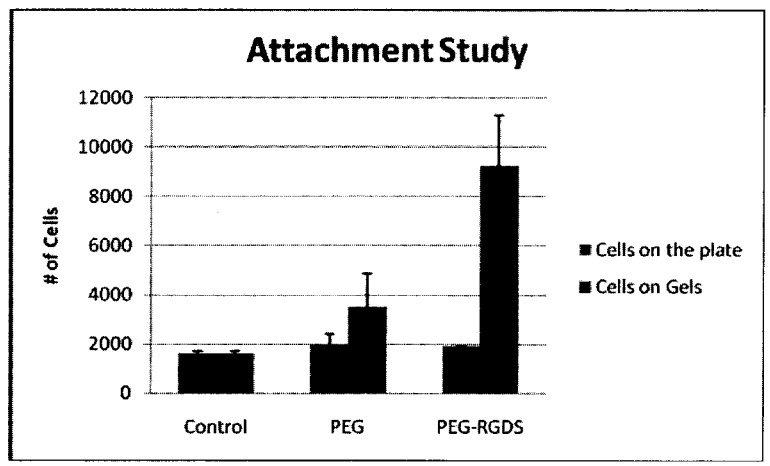
FIG. 6: Attachment study indicating that on PEG-RGDS hydrogels ("RGDS" disclosed as SEQ ID NO: 1), RPE cells have a better attachment and proliferation rates then on PEG hydrogels without RGDS (SEQ ID NO:1). Cells on the plate are left bars and cells on gels are right bars.
Figure 7:
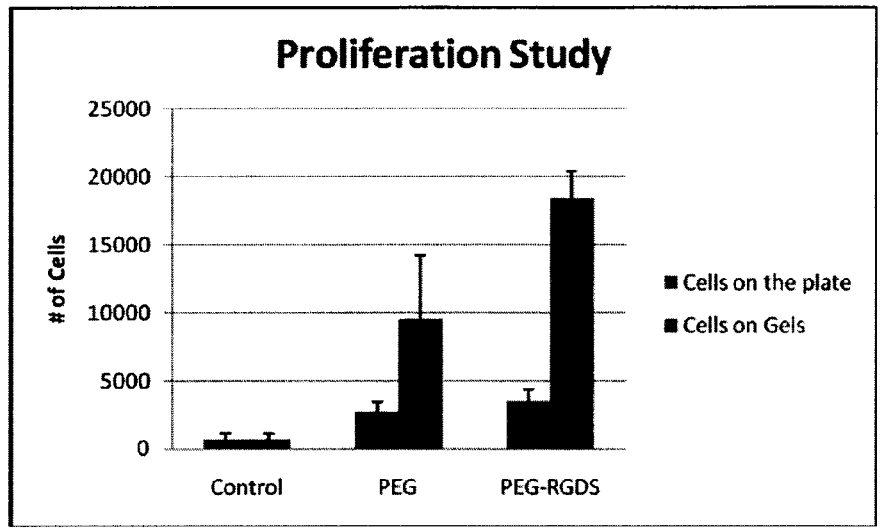
FIG. 7: Proliferation study indicating that on PEG-RGDS hydrogels ("RGDS" disclosed as SEQ ID NO: 1), RPE cells have a better attachment and proliferation rates then on PEG hydrogels without RGDS (SEQ ID NO:1). Cells on the plate are left bars and cells on gels are right bars.
Figure 8:
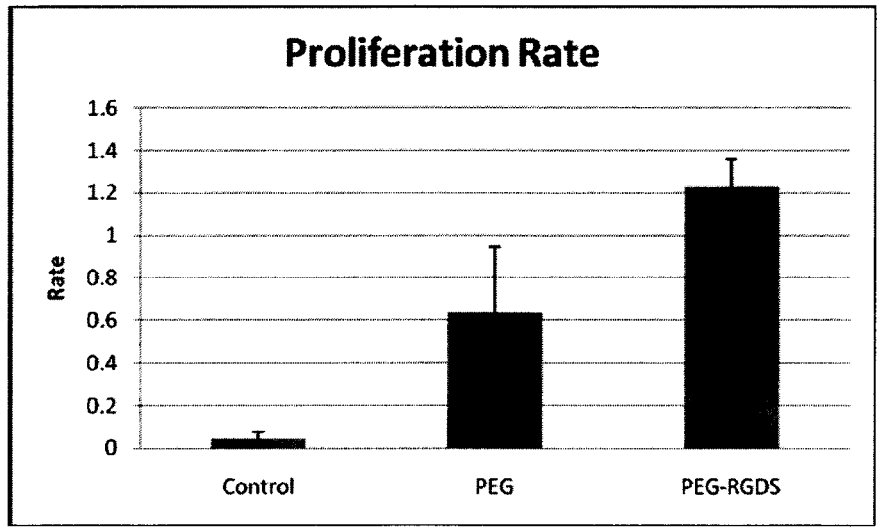
FIG. 8: Proliferation study indicating that on PEG-RGDS hydrogels ("RGDS" disclosed as SEQ ID NO: 1), RPE cells have a better attachment and proliferation rates then on PEG hydrogels without RGDS (SEQ ID NO:1).
Figure 10:
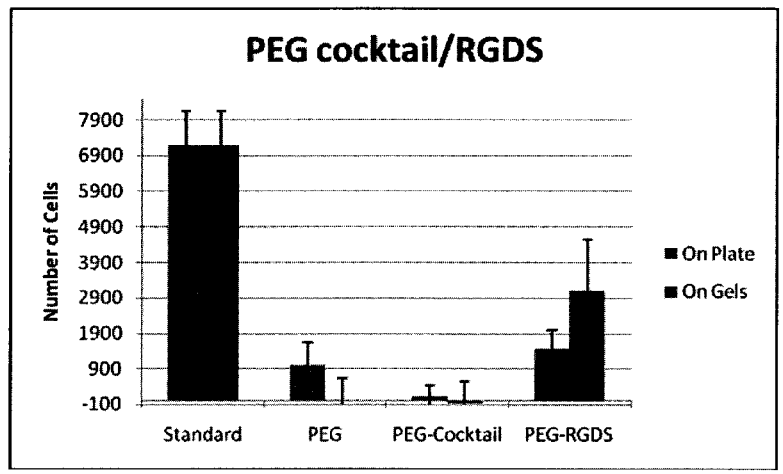
FIG. 10: The RGDS (SEQ ID NO:1) supplementation resulted in a better reattachment rate than ECM-P cocktail on PEG hydrogels. Cells on the plate are left bars and cells on gels are right bars.
Figure 11:
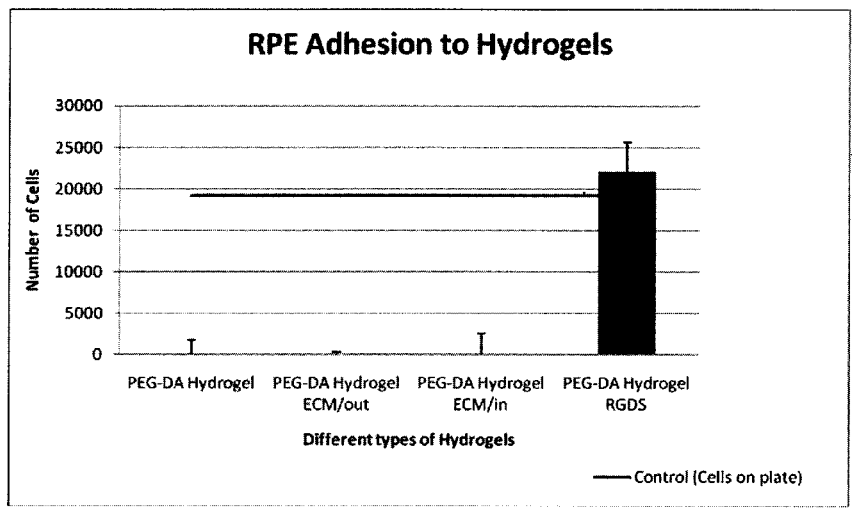
FIG. 11: RPE attachment to PEG hydrogels with or without RGDS (SEQ ID NO:1) or with ECM cocktail coated or incorporated. Results are averages with standard deviations.
Figure 12:
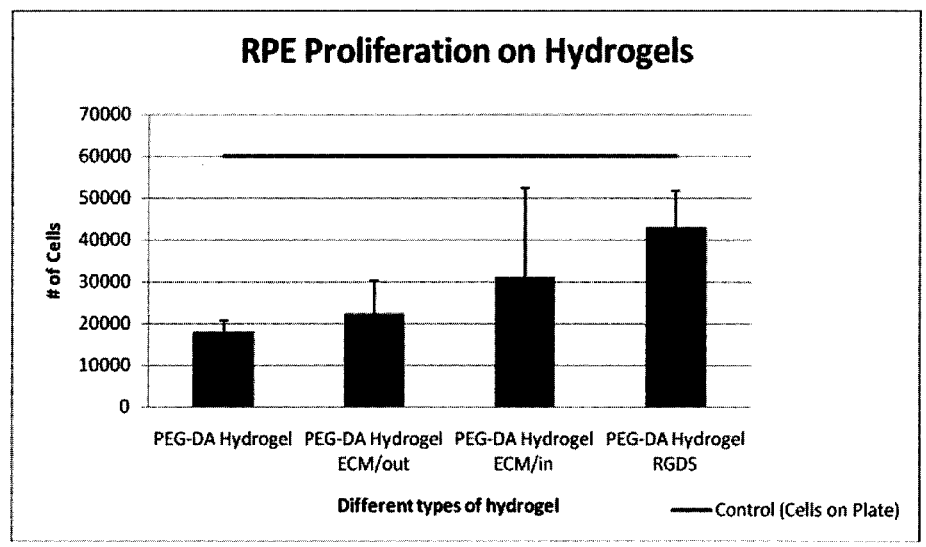
FIG. 12: RPE proliferation to PEG hydrogels with or without RGDS (SEQ ID NO:1) or with ECM cocktail coated or incorporated. Results are averages with standard deviations.
Figure 13:
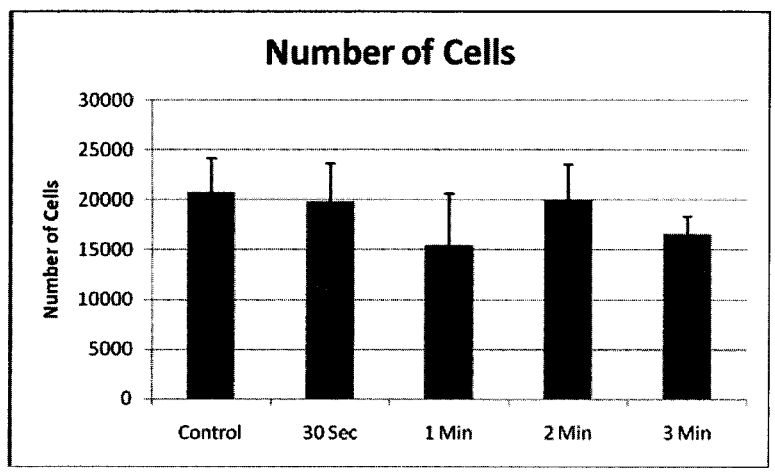
FIG. 13: Results indicating that exposure to UV at the time and strength required to polymerize the hydrogel did not affect the RPE cells loaded up with magnetic beads.
Figure 14:
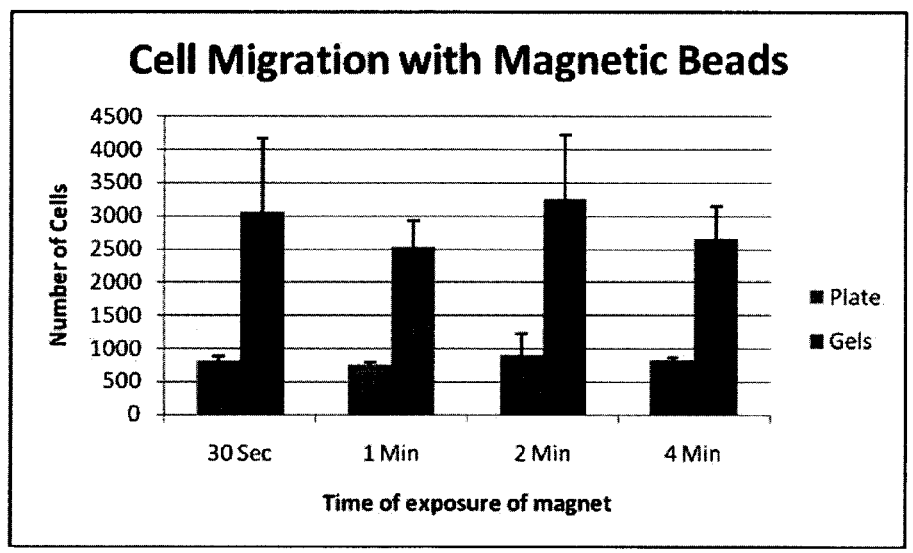
FIG. 14: Results indicating that RPE cells do not migrate through the gel. This result demonstrates the safety of the procedure by demonstrating that entrapped RPE cells will not migrate into the ocular tissues and form fibrotic scars that may lead to vision loss. Cells on the plate are left bars and cells on gels are right bars.

Objective:
To assess if RPE cells can adhere to designed hydrogels and after attachment proliferate.
Protocol:
Hydrogels with RGDS (SEQ ID NO:1) adhesion ligands were prepared. Hydrogels without RGDS (SEQ ID NO:1), hydrogels coated with ECM-P cocktail (laminin (330 µg/ml), fibronectin (250 µg/ml), and vitronectin (33 µg/ml)), and hydrogels with the ECM-P cocktail polymerized within were used as controls. The hydrogels were allowed to swell to equilibrium overnight and ARPE-19 (ATCC) cells are then seeded upon the surface at 46785 cells/cm$^2$. After 24 (attachment) and 48 (proliferation) hours, surfaces were rinsed and RPE cells counted via MTS assay.
Results:
It was found that RPE cells did not adhere to the hydrogels without RGDS (SEQ ID NO:1), simply coated with ECM-P cocktail, or with ECM-P cocktail within the hydrogels. However, cells were able to adhere to hydrogels with RGDS (SEQ ID NO:1) (FIG. 3). After 48 hours, it was observed that the cells were able to proliferate more on the hydrogels with RGDS (SEQ ID NO:1) (FIG. 4). It was observed during these studies the RPE used can become non-attachment dependent and grow as suspended spheroid colonies, which explains the increase in number of cells on the controls.

Example 3

The efficacy and optimal concentrations of specific peptide motifs, such as RGDS (SEQ ID NO:1), YIGSR (SEQ ID NO:2), KQAGDV (SEQ ID NO:3), and growth factors, such as bFGF and PDGF, in promoting RPE reattachment, survival, growth and differentiation will be determined.

Adhesion peptide ligand(s) and growth factors will be grafted into the hydrogel, and RPE adhesion, survival, repopulation and differentiation will be investigated. The cell adhesion ligands are short peptide sequences derived from ECM-P. Ligands to be investigated are RGDS (SEQ ID NO:1) (derived from fibronectin and collagen), YIGSR (SEQ ID NO:2) (derived from laminin) and KQAGDV (SEQ ID NO:3) (derived from fibrinogen), or combinations of these ligands. Platelet derived growth factor (PDGF), basic and acid fibroblast growth factor (bFGF and aFGF, respectively), insulin-like growth factor (IGF), and epidermal growth factor (EGF) stimulate RPE cell DNA synthesis and initiate migration. Additionally, PDGF and bFGF had a synergistic effect on cell proliferation. Studies conducted with these factors, such as PDGF and bFGF, will examine the effects individually and in combination. Within this example, studies will be conducted with adhesion ligands and growth factors independently first, then combined.

Hydrogel Preparations

Laminin, vitronectin and fibronectin matrix proteins may stimulate adhesion. The initial adhesion peptide ligand to be investigated will be Arg-Gly-Asp-Ser (RGDS) (SEQ ID NO:1). Adhesive ligand peptide sequences will be covalently attached to the PEG hydrogel through a PEG linker chain. To conjugate the target to the linker chain, a simple peptide bond will be made between the amino terminus (or any other primary amine) and the activated carboxylic group of the acryloyl-PEG-NHS(N, hydroxysuccinimide).

In the case of adhesion ligands, a 1:1 molar ratio will be used due to the availability of a single amine on the sequence. Unconjugated peptides will be separated by dialysis. Coupling efficiency will be determined through gel permeation chromatography equipped with UV (260 nm) and evaporative light scattering detectors (GPC/ELS). Acryloyl-PEG-NHS molecular weight is 3400 Da (Laysan Bio, Inc.; Arab, Ala.). To deliver the growth factors to the cells, the growth factors will be covalently grafted into the hydrogels, thus activation only occurs when the cell encounters the growth factor as it migrates across the hydrogel substrate. To graft the growth factor into the hydrogel similar protocols will be followed as described above. However, the growth factor to acryloyl-PEG-NHS mole ratio will be increased to ensure PEG conjugation. For example, bFGF has previously been conjugated to PEG using a 1:15 ratio of FGF:PEG.

Hydrogels can be prepared by combining 0.1 g/ml PEG diacrylate, with acryloyl-PEG-adhesion ligand and/or acryloyl-PEG-growth factor in 10 mM HEPES buffered saline (pH 7.4). The solution will then be filter sterilized and 10 µl/mL of 2,2-dimethyl-2-phenyl-acetophenone in n-vinylpyrrolidone (600 mg/ml) will be added as the photoinitiator. The resulting solution will then be placed in a mold and exposed to UV light (365 nm, 10 mW/cm$^2$) for 30 seconds to convert the liquid polymer to a hydrogel through a Michael-type addition reaction (Gobin et al., *FASEB J.*, 16, 751-753 (2002). Due to the fast polymerization time (<1 min), studies will have a homogenous concentration of adhesion ligand and growth factor. This polymerization protocol (polymer monomers, photoinitiator and UV light wavelength and intensity) has been shown to be non-toxic to RPE cells and other surrounding ocular cells (Gobin et al., *FASEB J.*, 16, 751-753 (2002); and Mann et al., *Biomaterials*, 22, 3045-3051 (2001)).

Cell Models

Human RPE cells (ARPE-19, ATCC, Manassas, Va.), that have morphologic and functional characteristics similar to those of adult human RPE cells, will be used for the adhesion and growth studies. ARPE-19 will be maintained in a 1:1 mixture of DMEM and Ham's F-12 media with 10-20% fetal bovine serum.

RPE Attachment and Viability

Hydrogels with various concentrations of ligands will be photopolymerized in tissue culture well plates. Two positive controls will be used (1) bovine cornea endothelial matrix-coated untreated tissue culture plates, (2) well coated with PEG polymer mixed with laminin (330 μg/ml), fibronectin (250 μg/ml), or vitronectin (33 μg/ml). Synchronized RPE cells, via serum deprivation, will be plated at approximately 15% confluency and allowed to attach for 24 hrs. The number of attached live RPE cells will be determined with a colorimetric assay (CellTiter 96 Aqueous proliferation assay; Promega, Madison, Wis.). Apoptosis rates will also be assessed using a TUNEL assay (APO-BrdU TUNEL Assay with Alexa Fluor, Molecular Probes, Eugene, Oreg.).

RPE Morphology

The RPE morphology, during resurfacing and after monolayer coverage, will be assessed using scanning electron microscopy, immunohistochemistry and biochemical analysis. To assess cytoskeleton reorganization, cells will be stained to visualize actin cytoskeleton and tight junction formations (zonula occluden 1; ZO-1). Actin reorganization occurs in RPE cells at the wound edge, with fibers oriented parallel to the movement into the defect area. After reestablishment of a monolayer, the cytoskeleton reorganizes again to form bundles of actin as belts around the cells. The tight junctions are important in defining the apical and basolateral membrane domains and thus maintenance of proper cell orientation due to polarized distribution of plasma membrane proteins. To evaluate differentiation, the cells will be stained for α-smooth muscle actin, expressed only in dedifferentiated cells, and cytokeratin-18, as a differentiation marker. Also, differentiation will be determined by RPE65 and cellular retinaldehyde binding protein expression as well as polarized distribution of Na—K ATPase pump.

RPE Metabolism

To examine metabolism of the RPE cells, a phagocytic activity assay will be performed (Lu et al., *Biomaterials*, 28, 1486-1494 (2007); Lee et al., *Biomaterials*, 28, 2192-2201 (2007); Chaitin et al., *Invest Ophthalmol Vis Sci*, 24, 812-820 (1983)). Phagocytosis of outer segments is essential to the renewal of photoreceptors. Rod outer segments will be isolated from porcine retinas and fluorescein labeled. A suspension of the outer segments will then be incubated with the RPE cells for 3, 10, or 24 hrs at 37° C. Cells will then be fixed, but not permeabilized, and stained for extracellular bound outer segments using a primary antibody to rhodopsin and a TRITC labeled secondary antibody. Nuclei will be identified with DAPI staining. Images will then be acquired using epifluorescence microscopy (EH-2, Olympus, Japan) and Metamorph software. Both bound and internalized outer segments will be quantified.

All studies will be conducted in at least triplicate and will be statistically analyzed using Minitab 16 Statistical software with a $p$-value$<0.05$ considered significantly different.

Example 4

Assessment of Performance of Biomatrix within an Organ Model

Studies planned for this specific aim represent in vivo conditions. For this purpose, an organ culture method using human donor eyes obtained from elderly donors and donors with age-related macular degeneration will be used. This model will allow testing of the efficacy of the hydrogel to cover the defects and allow RPE cells to populate them. During these experiments, explants of human Bruch's membrane will be isolated and a defect exposing the inner collagen layer will be made. The hydrogel prepolymer will then be polymerized on the defect. Adhesion, survival growth, differentiation and function of the seeded RPE will then be assessed.

Harvesting of Human Bruch's Membrane Explants

Explants of inner collagen layer of human Bruch's membrane will be prepared from the periphery of elderly (>65) donors and donors with AMD within 24 hours of death. Harvesting technique was described previously (Tezel et al., *Investigative Ophthalmology & Visual Science*, 40, 767-774 (1999)). Briefly, a full thickness circumferential incision will be made posterior to the ora serrata and the anterior segment and vitreous will be removed. The posterior pole of each eye cup will be inspected visually with direct and retroillumination under a dissecting microscope and globes will be discarded if there will be any evidence of subretinal blood, previous surgery or any extensive structural or vascular alteration of the posterior segment due to a disease process, such as proliferative diabetic retinopathy or proliferative vitreoretinopathy. The eyecups will be put in carbon dioxide-free media and a scleral incision will be made 3 mm from the limbus and extended 360 degrees. Four radial incisions will then be made and the sclera will be peeled away. A circumferential incision will be made into the subretinal space 1 mm posterior to the ora serrata. The choroid-Bruch's membrane-RPE complex will be then carefully peeled towards the optic disc and removed after trimming its attachment to the optic nerve. The Bruch's membrane explant will then be floated in CFM over a 12-18 micron thick hydrophilic polycarbonate-polyvinylpyrrolidone membrane with 0.4 μm pores (Millipore, Bedford, Mass.) with the basal lamina facing towards the membrane. Thus exposed Bruch's membrane explants will be stabilized on 4% agarose in 96-wells and their defects will be covered with the hydrogel. RPE survival and ability to populate treated explants will then be studied by plating RPE cells onto hydrogel-coated Bruch's membrane explants. Untreated aged Bruch's membranes and membranes coated with extracellular matrix proteins will be used as controls.

RPE Cell Behavior

Second passage RPE cells will be plated onto coated aged-Bruch's membrane explants. Reattachment, survival, growth, repopulation, differentiation and function of RPE cells will be studied as is described. RPE cells seeded onto untreated and extracellular matrix protein-coated Bruch's membranes will be used as controls.

Example 5

Assess Performance of Hydrogels in an In Vivo Porcine Model

Biomimetic hydrogels containing adhesion ligands and/or growth factors will be assessed in a porcine model. Hydrogels will be polymerized in situ and qualitative and quantitative characterization of RPE wound healing will be assessed.

Porcine Model

For this purpose, a model described by Kiilgaard and colleagues will be used (Kiilgaard et al., *Acta Ophthalmol Scand*, 83, 697-704 (2005)). Adult domestic pigs (*Sus domestica*) will undergo a three-port localized vitrectomy. Access to the subretinal space will be made with a retinal perforator (Synergetics, Mo., USA). Retina will then be carefully detached by injecting isotonic NaCl (0.9%) through a 30G needle (Ref 1270, DORC, Zuidland, Holland). An automated scissor (Storz, St. Louis, Mo.) will be used to enlarge the retinotomy before the gentle removal of the RPE using a retinal scraper (DORC). The subretinal space will then be washed with isotonic NaCl through a 20G subretinal cannula (#5021, Visitec, Fla.) to ensure total removal of the damaged RPE. Finally, the Bruch's membrane will be damaged by scraping and rupturing with a retinal perforator. Hydrogel prepolymer will then be injected into the damaged space and photopolymerized. Treated eyes will be followed up by ophthalmoscopy, fundus photography and fluorescein angiography to determine the ingrowth of choroidal membrane. At 1, 2, and 4 weeks, treated eyes will be enucleated, fixed in Lilly's fluid (Bie & Berntsen, Rodovre, Denmark), and embedded in paraffin. Sections will be stained with hematoxylin and eosin and then examined by light microscopy in order to define the three dimensional structure.

Example 6

It has been determined that PEGDA hydrogels maintain their structure and composition over 3 weeks. RPE cells are stable when exposed to the wavelength of light needed for hydrogel formation. PEGDA hydrogels support RPE attachment.

Cell Maintenance:

RPE cells were cultured in DMEM media with 5% fetal bovine serum. Cells were maintained at 37° C. with 5% $CO_2$.

Hydrogel Preparation:

PEGDA and HA were dissolved in PBS at 37° C. in separate wells for 2 hours. PEGDA was then mixed gently with the HA and incubated for an additional 30 minutes to help remove bubbles. PEGDA hydrogels were prepared by dissolving 0.1 mg/ml polymer in 1 ml PBS. The photoinitiating acetophenone solution (10 µl/ml) was then added and allowed to mix through diffusion for an hour. The prepolymer solutions were then photopolymerized by exposure to UV light (365 nm, 10 $mW/cm^2$) which converts it to hydrogels.

UV Cell Death:

RPE cells were seeded in 96-well plate at 15,000 cells/ml (n=5) until were confluent. They were exposed to UV light for 30 secs, 1 min, 2 mins, and 3 mins at 7 cm and were compared to cells not exposed to UV light. Cell death was measured by MTS assay right after time of exposure.

RPE Attachment on Hydrogels with RGDS (SEQ ID NO:1):

Hydrogels were prepared as previously described but with 1:1 ratio of acryloyl-PEG-RGDS ("RGDS" disclosed as SEQ ID NO: 1). After initial swelling in PBS for 24 hrs, RPE cells were seeded on surface at 15,000 cells/ml (n=3). Control include: cells on the 96-well plate, cell on hydrogel without RGDS (SEQ ID NO:1), and cells on hydrogel with RGDS (SEQ ID NO:1).

Results:

Prepared hydrogels were clear and transparent. Hydrogels initially swelled to equilibrium over 24 hours. The RPE cell attachment was significantly greater on hydrogels with RGDS (SEQ ID NO:1) adhesion ligands as compared to control, cells on a plate, and just PEG. After exposure to UV light, it was observed that there was no cell death from the given time constraints.

Example 7

Cell Morphology after 24 Hours

Rationale:

Cells on hydrogels with 2.9 µmol/mL RGDS (SEQ ID NO:1) have shown good cell adhesion after 24 hours, but the morphology was not determined.

Hypothesis:

RGDS (SEQ ID NO:1) adhesion ligand is sufficient to maintain RPE morphology and not initiate dedifferentiation of the cells.

Methods:

Hydrogels were made as previously described with 2.8 RGDS (SEQ ID NO:1). 15,000 RPEs were seeded on surface. Cells were imaged in phase contrast at 10× magnification after 24 hrs.

Results:

It was observed that RPEs had similar morphology to that cells grown on tissue cultured treated surfaces.

Conclusions:

Cells can adhere and maintain similar morphology as on normal tissue culture surfaces.

Example 8

Cell Area after 6, 24 and 48 Hrs Adhesion

Rationale:

As adhesivity increases, cells are more likely to spread because they cannot break the many adhesion connections made. Hence, cell function may be significant reduced (Gobin et al., FASEB Journal (2002) 16; 7:751-753 (*The FASEB Journal* express article 10.1096/fj.01-0759fje)).

Hypothesis:

As the adhesion ligand concentration increases, the cell area will also increase.

Methods:

Hydrogels were made as previously described with desired concentrations of RGDS (SEQ ID NO:1) (2.8-5.0 µmol/ml). Cells were seeded at 15% confluency. At 6, 24 and 48 hrs, surfaces were imaged in phase contrast, and the area of cell coverage within the field of view was determined and normalized by the number of cells present. Area is presented as pixel area. Controls were traditional culture surfaces, as well as PEGDA hydrogels alone.

Results:

Cells on PEGDA are small and rounded. With increasing concentration, no differences in cell areas were observed. Cell area increases over the initial 24 hours, but then levels of afterwards.

Conclusions:

Though increasing ligand concentration can increase the rate of adhesion, it does not significantly alter the cell area/morphology. Cells are most likely to perform and function as normal healthy cells.

Example 9

Cell Attachment and Morphology on Higher Concentrations at 15, 30, 120 Minutes and 6 Hours Rationale:

During surgery, the patient may not be exposed to long hours waiting for cells to adhere. Hence, in order to develop a method for the cell transplantation, the minimum amount of time needed for cell adhesion was examined.

Methods:

Hydrogels with 5.0 µmol/ml RGDS (SEQ ID NO:1) were made. Cells were seeded at 15% confluency. Number of cells attached was determined using CyQuant DNA assay. Evaluation was at 15, 30 and 120 minutes as well as 6 hours.

Results:

Currently only the 15 minute results are complete. It was found that no or little cells adhered to the hydrogel surfaces.

Conclusion:

More time than 15 minutes may be needed to allow cells to diffuse to the surface and adhere to the presented adhesion ligands. Increased times are currently under investigation.

Example 10

Cell Growth Rate

Rationale:

Hydrogels may present only one type of adhesion ligand to the cells to initiate adhesion and signal growth. Though cells are adhering and growing, their growth rate needs to be determined.

Results:

The RPEs proliferate at a slower rate on the hydrogels with lower concentrations of RGDS (SEQ ID NO:1) as compared to the controls. The fibronectin-coated glass slides and non-coated glass slides had doubling times of 47 hours and 52 hours, respectively. The 2.8, 3.9, and 5.0 μmol/L PEG-RGDS (SEQ ID NO:1) hydrogels had doubling times of 76, 78, and 58 hours, respectively.

Example 11

Cell Attachment and Growth on Different Stiffness

RPE cell attachment and growth is currently being studied on hydrogels where the hydrogel stiffness has been modified. Aged Bruch's membrane is highly crosslinked, thus increasing matrix stiffness. Thus the hydrogel elastic modulus (stiffness) will be measured using rheology and AFM and compared to healthy, young, and aged membranes. Hydrogel stiffness will be modulated by changing polymer concentration (e.g., from 0.05-3.0 g/mL, e.g., 0.05, 0.1, 1.5, 2.0, and 3.0 g/mL) and/or changing polymer molecular weight (~3000-10,000 Da, e.g., about 6000 Da).

Example 12

Force to Delaminate Hydrogel from Tissue

To confirm that hydrogel material is not delaminate from the damaged tissue surface, mechanical testing will be used to evaluate what forces are needed to separate the hydrogel from the tissue surface. Delamination will be examined by tensile and shear forces.

Example 13

Rationale:

RPE cells are attachment-dependent cells. Once cells are lifted off from their matrix, apoptotic cell death mechanisms can be triggered. Apoptosis of the cell can only be stopped if the cell reattaches to a matrix through appropriate ligands (Tezel et al., *Graefes Arch Clin Exp Ophthalmol.* 1997 January; 235(1):41-7). RPE cell attachment is mediated mainly through the integrins expressed on the cell membrane and their ligand on the matrix. The RGDS (SEQ ID NO:1) polypeptide can interact with integrins and anchor the cell to the matrix. Thus, enriching the hydrogel with RGDS (SEQ ID NO:1) may enhance the attachment and survivability of the plated RPE cells.

Question:

Would PEG-RGDS hydrogels ("RGDS" disclosed as SEQ ID NO: 1) have a better attachment and proliferation rate then just PEG hydrogels?

Hypothesis:

PEG-RGDS hydrogels ("RGDS" disclosed as SEQ ID NO: 1) have a better attachment and proliferation rate then just PEG hydrogels.

Method:

In 15 ml centrifuge tube the following were combined: 0.1 g PEG Diacrylate, desired amount of PEG-RGDS (concentration of 3 μmol was used) ("RGDS" disclosed as SEQ ID NO: 1) and 1.0 ml PBS buffer. The solution was filter sterilized. 10 μl of acetophenone solution (590 mg/ml in pyrrolidinone) was added. Mix gently by swirling—make sure no bubbles are made. In a separate 15 ml centrifuge tube the following were combined: 0.1 g PEG Diacrylate, and 1.0 ml PBS buffer. 10 μl acetophenone solution (590 mg/ml in pyrrolidinone) was added. Mix gently by swirling—make sure no bubbles are made. 50 μl of each solution was added in two 96 well plates (non-tissue cultured) for attachment and proliferation, n=5. Place under UV (365 nm, 10 mW/cm$^2$) lamp to crosslink (30 sec-2 Min). The hydrogel was removed from the mold or well using a spatula and placed in another well. Media or buffer was added to allow gels to swell for 24 hours. ARPE-19 cells (n=15,000) in 100 μl media were added onto the surface of the gels. The RPE reattachment rate was determined 24 hours later and the proliferation was determined 48 hours later using MTS assay.

Result:

A standard curve was created to determine the number of cells on the gels. Also, the gels were removed and placed a different well to get the reading of just the gels. Cells adhere to hydrogels containing RGDS (SEQ ID NO:1), but there is significantly less on the control and PEGDA hydrogel. Cells are capable of proliferating on the hydrogels with RGDS (SEQ ID NO:1).

Conclusion:

On PEG-RGDS hydrogels ("RGDS" disclosed as SEQ ID NO: 1), RPE cells have a better attachment and proliferation rates then on PEG hydrogels without RGDS (SEQ ID NO:1).

Example 14

Rationale:

RPE reattachment suppress apoptosis. Higher reattachment is important for the grafted cells to populate the denuded Bruch's membrane faster and to support photoreceptor cells for the restoration of the central sight. As described herein, RGDS (SEQ ID NO:1) plays a role in RPE cell reattachment. The optimal concentration of RGDS (SEQ ID NO:1) polypeptide to maximizes RPE reattachment for maculoplasty was investigated.

Question:

What should be the optimal concentration of RGDS (SEQ ID NO:1) to support RPE cell attachment and survival?

Hypothesis:

Increasing concentrations of RGDS (SEQ ID NO:1) will increase RPE cell attachment until it saturates the receptors.

Methods:

PEG hydrogels containing 2.8-15 μmol/ml of RGDS (SEQ ID NO:1) were prepared as described. 15,000 viable RPE cells were plated and RPE adhesion was assessed 30 and 120 minutes.

Result:

RPE reattachment increased with increasing concentrations of RGDS (SEQ ID NO:1). Concentrations higher than 5.0 μmol/ml did not effect RPE reattachment significantly.

Conclusion:

An optimum concentration of RGDS (SEQ ID NO:1) to support RPE reattachment is 5.0 μmol/ml.

Example 15

Rationale:

RPE cell reattachment and survival on aged Bruch's membrane can be improved by using an ECM-P cocktail (Tezel et al., Invest Ophthalmol Vis Sci. 2004; 45(9):3337-48).

Question:

Would an ECM-P cocktail be better than RGDS (SEQ ID NO:1) in cell attachment on PEG hydrogels?

Hypothesis:

The RGDS (SEQ ID NO:1)-enrichment will create comparable or better RPE reattachment rates than ECM-P addition.

Methods:

In 15 ml centrifuge tubes the following were combined: 0.1 g PEG Diacrylate (PEGDA), desired amount of PEG-RGDS ("RGDS" disclosed as SEQ ID NO: 1) (when using the ECM-P cocktail, PEG-RGDS ("RGDS" disclosed as SEQ ID NO: 1) is not added to the mix) and 1.0 ml PBS buffer. Filter sterilize the solution. Add 10 µl acetophenone solution (590 mg/ml in pyrrolidinone). Mix gently by swirling, making sure no bubbles are made. Add 50 µl of the solution in 96 well plate (tissue cultured), n=3. Place under UV lamp to crosslink (30 sec-2 Min). Remove hydrogel from mold or well using a spatula and place in another well. Add media or buffer to allow gels to swell for 24 hours. After swelling coat the PEGDA gels with the ECM-P cocktail mix: laminin (330 µg/ml), fibronectin (250 µg/ml), and vitronectin (33 µg/ml). Incubate the coated gels for 30 minutes at 37° C. Next, ARPE-19 cells (n=15,000) in 100 µl media, were plated onto the surface of the gels and the RPE reattachment was determined 24 hours later using MTS assay.

Result:

In the study, the control was just cells on the plate, just regular hydrogels, hydrogels with RGDS (SEQ ID NO:1), and hydrogels with the ECM-P cocktail mix. The hydrogels were removed before the MTS assay and placed in a separate well so we can get a reading of just the gels.

|  | Average on Plate | Stdev | Average on Gels | Stdev |
| --- | --- | --- | --- | --- |
| Standard | 7188 | 944 | | |
| PEG | 1003 | 639 | 11 | 609 |
| PEG-Cocktail | 133 | 281 | −53 | 600 |
| PEG-RGDS ("RGDS" disclosed as SEQ ID NO: 1) | 1468 | 528 | 3096 | 1457 |

Conclusion:

The hypothesis was correct. The RGDS (SEQ ID NO:1) supplementation resulted in a better reattachment rate than ECM-P cocktail on PEG hydrogels.

Example 16

Rationale:

RPE attachment is a critical step in populating the aged Bruch's membrane; however, attached ells have to undergo mitotic cell division to cover the denuded surface. Previous work demonstrated that ECM-P coating can enhance RPE survival and proliferation rate. Thus, it is important to gauge the effect of RGDS (SEQ ID NO:1)-enrichment on RPE proliferation rate in comparison with ECM-P coating.

Question:

Can RGDS (SEQ ID NO:1)-enrichment of PEG hydrogels achieve a comparable or better proliferation rate than ECM-P supplementation of the PEG hydrogels?

Hypothesis:

RGDS (SEQ ID NO:1)-enrichment of PEG hydrogels can result in comparable proliferation rates on PEG hydrogels as ECM-P supplements.

Methods:

Hydrogels with RGDS (SEQ ID NO:1) adhesion ligands were prepared. Hydrogels without RGDS (SEQ ID NO:1), hydrogels coated with ECM-P cocktail (laminin (330 µg/ml), fibronectin (250 µg/ml), and vitronectin (33 µg/ml)), and hydrogels with the ECM cocktail polymerized within were used as controls. The hydrogels were allowed to swell to equilibrium overnight and ARPE-19 (ATCC) cells were then seeded upon the surface at 46785 cells/cm$^2$. After 24 (attachment) and 48 (proliferation) hours, surfaces were rinsed and RPE cells were counted via MTS assay.

Results:

RPE cells adhere poorly onto the hydrogels without RGDS (SEQ ID NO:1), simply coated with ECM-P, or with ECM-P premixed with hydrogels. However, cells were able to adhere to hydrogels with RGDS (SEQ ID NO:1). After 48 hours, cells were able to proliferate more on the hydrogels with RGDS (SEQ ID NO:1).

Conclusion:

Both RPE cells attachment and proliferation rates are enhanced with addition of RGDS (SEQ ID NO:1) to PEG. RPE resurfacing is better on RGDS (SEQ ID NO:1)-supplemented PEG hydrogels compared with ECM-P addition.

Example 17

Rationale:

RPE cells population may involve transplantation and/or seeding of RPE or stem cells harvested from the patient or a cadaver. Maintaining proper positioning of the cells in close proximity with the hydrogel will be important for subsequent cell attachment and survival. This will also avoid spilling of the cells into the ocular cavities, such as vitreous, and forming in fibrotic membranes. This may be achieved by transplanting the cells within the PEG into the subretinal space and positioning them to the inner surface prior to polymerizing the PEG into hydrogel. Movement of the RPE cells within the PEG can be controlled using an electromagnetic field. For this purpose, RPE cells can be loaded up with magnetic beads prior to transplantation and a magnetic field can be applied to pull them on to the inner surface of the gel before polymerization with UV. However, the toxicity of UV exposure to RPE cells must be determined to assess the feasibility of this technique.

Questions:

Would exposing ARPE-19 cells with magnetic beads to UV light for short time length affect RPE cell viability?

Hypothesis:

Exposing the ARPE-19 cells with magnetic beads during the polymerization of the PEG will not affect RPE cell viability.

Method:

In a 15 ml centrifuge tube, the cell concentration of APRE-19 cells was 150000 cells/ml. 10 ul of magnetic beads was added to 1 ml the cell concentration media. Mix gently by swirling—made sure no bubbles are made. 100 ul was added to a 96 well plate for n=5 for control, 30 secs, 1 min, 2 mins, and 3 mins. When the cells are confluent, the MTS assay was run.

Result:
Exposing ARPE-19 cells to UV light at a distance of 7 cm for 30 seconds to 3 minutes during gel polymerization did not affect RPE cell viability (99.4±0.1% vs. 99.6±0.5% for 30 seconds, p=1.0)

|  | Average | Stdev |
|---|---|---|
| Control | 20843 | 3311 |
| 30 Sec | 19891 | 3770 |
| 1 Min | 15531 | 5036 |
| 2 Min | 20120 | 3459 |
| 3 Min | 16620 | 1690 |

Conclusion:
Exposure to UV at the time and strength required to polymerize the hydrogel did not affect the RPE cells loaded up with magnetic beads.

Example 18

Rationale:
Polymerization of the PEG hydrogel occurs by cross-linking of PEG polymers under UV light. Several other dyes have been used to substitute for UV light. Use of non-UV sources was also tested due to safety issues.
Question:
Can PEG be polymerized using Rose Bengal or Eosin Y?
Hypothesis:
PEG polymerization with Rose Bengal or Eosin Y will not be as effective as UV-induced polymerization.
Methods:
Photodynamic cross-linking of PEG was attempted by adding of Rose Bengal (20 µM) or Eosin Y. Results were compared with UV-polymerization.
Results:
Both Rose Bengal and Eosin Y are capable of polymerizing PEGDA hydrogels. However, the time to crosslink is greater than 40 minutes, which is likely unacceptable for this application.
Conclusion:
UV apparently cannot be replaced by photodynamic cross-linking of PEG with Rose Bengal or Eosin Y.

Example 19

Rationale:
Polymerization of the hydrogel in the subretinal space will involve short-term exposure to UV light. Safety of this exposure on human photoreceptors will be determined before pursuing to in vivo experiments.
Question:
Can UV exposure during the polymerization process affect photoreceptor cell viability?
Hypothesis:
Short-term exposure to UV (365 nm, 7 cm away from source, ~10 mW/cm$^2$) during the polymerization process will not affect photoreceptor viability.
Methods:
Fresh (<24 hours) human cadaver eyes were obtained from a local eye bank. The neurosensory retina was removed and cut into rectangular sheets (10×15 mm) with a razor blade and placed on a hydrophobic membrane (HTTP, Millipore) with photoreceptor side facing up. PEG-hydrogel was polymerized using UV on the photoreceptors and cell viability was determined with ethidinium/calcein staining (LIVE/DEAD assay, Invitrogen) 30 minutes after the polymerization process. Control groups included untreated and UV exposed retina tissues. Statistical difference was sought using Student's t-test.
Results:
No significant viability differences were observed between groups (94.8±0.3% vs. 95.2±0.4%, p=1.0). UV treated photoreceptors maintained viability>95%.
Conclusion:
UV treatment during the course of polymerization of the hydrogel does not adversely affect photoreceptor cell viability.

Example 20

Rationale:
Once polymerized, the hydrogel will form a mesh with nanoscale fenestra. Mobilization and aligning of the RPE cells at the inner surface of the hydrogel may not be possible once PEG is polymerized into the hydrogel. It is important to know at what stage RPE cells should be directed to the surface. Also, cells entrapped within the matrix should not digest the hydrogel and migrate through it. Otherwise these migratory RPE cells may undergo epithelio-mesenchymal transition and form fibrotic membranes. Thus, the ability of RPE cells to migrate through the hydrogel should also be assessed.
Questions:
Can RPE cells migrate through the hydrogel once it is polymerized?
Hypothesis:
RPE cells do not migrate through the hydrogel once it is polymerized. Despite magnetized RPE cells are directed using a magnetic field, the majority of the cells will remain stuck within the hydrogel after it is polymerized.
Method:
In 15 ml centrifuge tubes the following were combined: 0.2 g PEG Diacrylate, desired amount of PEG-RGDS ("RGDS" disclosed as SEQ ID NO: 1) and 1.0 ml PBS buffer. The solution was filter sterilized. 10 µl acetophenone solution (590 mg/ml in pyrrolidinone) was added. Mix gently by swirling—make sure no bubbles are made. In a separate 15 ml centrifuge tube, the cell concentration of ARPE-19 cells at 15,000 cells/ml was obtained. 10 µl of magnetic beads was added to 1 ml the cell concentration media. Mix gently by swirling—made sure no bubbles are made. 50 µl of gel/polymer solution was added to a 96-well plate with 10 µl of the cell magnetic beads media. A magnet was applied underneath the 96-well plate and placed under UV lamp to crosslink. After 24 hrs, the MTS assay was used to calculate the migration of cells.
Result:
There were four plates created for this experiment for each time variable: 30 sec, 1 min, 2 mins, and 4 mins. Crosslink under the UV light was for 2 mins.

|  | Plate | Stdev | Gels | Stdev | % Migration |
|---|---|---|---|---|---|
| 30 Sec | 804 | 73 | 3062 | 1111 | 20% |
| 1 Min | 752 | 46 | 2536 | 387 | 17% |
| 2 Min | 907 | 320 | 3262 | 960 | 22% |
| 4 Min | 819 | 44 | 2656 | 499 | 18% |

Conclusion:
RPE cells do not migrate through the gel. This result demonstrates the safety of the procedure by demonstrating that entrapped RPE cells will not migrate into the ocular tissues and form fibrotic scars that may lead to vision loss. A current formulation is non-degradable, hence cells cannot migrate through the hydrogel. This means that RPE cannot migrate out and vascular or immune cells cannot migrate in.

Example 21

Future Studies a) Examination of other ECM adhesion ligands
   a. RGDS (SEQ ID NO:1)+PHSRN (SEQ ID NO:8) (fibronectin and synergy site from fibronectin)
   b. YIGSR (SEQ ID NO:2) (laminin, basement membrane protein)
b) Examination of cell contractile force on hydrogels
   a. To assess material mechanical properties (at the cellular scale, μm) and cell contractile forces, atomic force microscopy will be used.
c) Effects of cell seeding density on attachment and function
   a. RPE cell behavior is dependent on cell number. Seeding density will be investigated to assess attachment, growth and repair can be enhanced by initial cell number.
d) Cell transplantation mechanisms
   a. In order to improve the success of transplanting the right cells in the correct location different methods of delivery of cells will be investigated and how these methods enhance cell attachment without interfering in subsequent survival and functionality will be assessed.
e) Cell functionality and cell-cell communication
   a. The ability to perform their function as a monolayer is formed will be assessed.
   b. Cell-cell communication will be evaluated
f) Studies with primary cells
   a. Currently all studies are with transformed ARPE-19 cells. Once optimal formulation has been narrowed, studies will be repeated with primary cells.
g) Ex-vivo studies
   a. Damaged Bruch's membrane will be used for evaluation.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A method for treating a disorder of the retina in a patient in need of such treatment, comprising administering to the patient a therapeutically effective amount of an in situ polymerizable poly(ethylene glycol) (PEG) based diacrylate hydrogel that comprises at least one adhesion ligand and polymerizing the hydrogel with UV light.

2. The method of claim 1, wherein the disorder of the retina is age-related macular degeneration (AMD), choroidal ruptures, angioid streaks, myopic maculopathy, presumed ocular histoplasmosis, globe ruptures, penetrating injuries, RPE and retinal atropies, degeneration or dystrophy.

3. The method of claim 2, wherein the disorder of the retina is AMD.

4. The method of claim 3, wherein the AMD is dry AMD.

5. The method of claim 3, wherein the AMD is wet AMD.

6. The method of claim 1 that further comprises performing a vitrectomy on the patient to remove subretinal scars.

7. The method of claim 1, wherein at least one adhesion ligand is covalently attached to the PEG hydrogel through a PEG linker chain.

8. The method of claim 1, wherein at least one adhesion ligand comprises the amino acid sequence RGDS (SEQ ID NO:1), YIGSR (SEQ ID NO:2), KQAGDV (SEQ ID NO:3), RGDV (SEQ ID NO:4), RGD-HYP (hydroxyproline) (SEQ ID NO:5), RGDT (SEQ ID NO:6) or VTCG (SEQ ID NO:7).

9. The method of claim 8, wherein at least one adhesion ligand is the amino acid sequence RGDS (SEQ ID NO:1), YIGSR (SEQ ID NO:2) or KQAGDV (SEQ ID NO:3).

10. The method of claim 9, wherein at least one adhesion ligand is the amino acid sequence RGDS (SEQ ID NO:1).

11. The method of claim 10, wherein the concentration of the adhesion ligand is about 5.0 µmol/ml.

12. The method of claim 10, wherein the hydrogel further comprises PHSRN (SEQ ID NO:8).

13. The method of claim 9, wherein at least one adhesion ligand is the amino acid sequence YIGSR (SEQ ID NO:2).

14. The method of claim 1, wherein the hydrogel further comprises at least one growth factor.

15. The method of claim 14, wherein the growth factor is bFGF, PDGF, hepatocyte growth factor (HGF), insulin-like growth factor (IGF) or epidermal growth factor (EGF).

16. The method of claim 1, wherein the hydrogel further comprises an anti-angiogentic or anti-apoptotic drug or cytokine.

* * * * *

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Tyr Ile Gly Ser Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Gln Ala Gly Asp Val
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gly Asp Val
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline

<400> SEQUENCE: 5

Arg Gly Asp Pro
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Asp Thr
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Thr Cys Gly
1

<210> SEQ ID NO 8
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro His Ser Arg Asn
1               5
```